United States Patent [19]
Gross et al.

[11] Patent Number: 5,981,743
[45] Date of Patent: Nov. 9, 1999

[54] CYCLIC ESTER RING-OPENED OLIGOMERS AND METHODS OF PREPARATION

[75] Inventors: Richard A. Gross, Chelmsford; Kirpal Bisht, Lowell; David Kaplan, Stowe, all of Mass.; Graham Swift, Blue Bell, Pa.; Fang Deng, Lowell, Mass.

[73] Assignee: University of Massachusetts, Boston, Mass.

[21] Appl. No.: 08/828,432

[22] Filed: Mar. 28, 1997

[51] Int. Cl.$^6$ .............................. C07H 1/00; C07G 17/00
[52] U.S. Cl. ...................... 536/123.1; 536/1.11; 536/4.1; 536/55.1; 536/115; 536/119; 536/124; 527/311; 527/314; 435/100; 435/101
[58] Field of Search .................................. 527/311, 314; 435/100, 101; 536/119, 115, 1.11, 55.1, 123.1, 124, 4.1

[56] References Cited

U.S. PATENT DOCUMENTS 5,270,421  12/1993  Dordick et al. .

OTHER PUBLICATIONS

Adelhorst et al., "Enzyme Catalysed Preparation of 6–O–Acylglucopyranesides", *Papers*, pp. 112–115 (1990).

Fabre et al., "Versatile Enzymatic Diacid Ester Synthesis of Butyl α–D–Glucopyranoside", *Tetrahedron*, 49(47): 10887–10882 (1993).

Fabre et al., "Regiospecific enzymic acylation of butyl α–D–Glucopyranoside", *Carbohydrate Research*, 243:407–411 (1993).

Henderson et al., "Enzyme–Catalyzed Polymerizations of ε–Caprolactone: Effects of Initiator on Product Structure, Propagation Kinetics, and Mechanism", *Macromolecules*, 29:7759–7766 (1996).

Knani et al., "Enzymatic Polyesterificiation in Organic Media", *Journal of Polymer Science*, 31(5):1221–1231 (1993).

MacDonald et al., "Enzyme–Catalyzed ε–Caprolactone Ring–Opening Polymerization", *Macromolecules*, 28:73–78 (1995).

Matsumura et al., "Enzymatic synthesis of novel vinyl monomers bearing β–D–Galactopyranoside residue", *Makromol. Chem., Rapid Commun.*, 14:55–58 (1993).

Patil et al., "Chemoenzymatic Synthesis of Novel Sucrose–Containing Polymers", *Macromolecules*, 24:3462–3463 (1991).

Ricardo et al., "Synthesis and Characterization of Glycoside Non–Ionic Surfactants", *Polymer Engineering and Science*, 36(2):182–187 (1996).

Riva et al., "Protease–Catalyzed Regioselective Esterification of Sugar and Related Compounds in Anhydrous Dimethylformamide", *J. Amn. Chem. Soc.*, 110:584–589 (1988).

Therisod et al., "Facile Enzymatic Preparation of Monoacylated Sugars in Pyridine", *J. Am. Chem. Soc.*, 108:5638–5640 (1986).

Therisod et al., "Regioselective Acylation of Secondary Hydroxyl Groups in Sugars Catalyzed by Lipases in Organic Solvents", *J. Am. Chem. Soc.*, 109:3977–3981 (1987).

Uyama et al., "Enzymatic Ring–Opening Polymerization of Lactones Catalyzed by Lipase", *Chemistry Letters*, 7:1149–1152 (1993).

*Primary Examiner*—James O. Wilson
*Attorney, Agent, or Firm*—Fish & Richardson P.C.

[57] ABSTRACT

An oligomer composed of a carbohydrate head group and an oligomer chain is disclosed. Methods for increasing the oligomerization rates of lactones and cyclic carbonates are also disclosed.

27 Claims, 8 Drawing Sheets

CYCLIC ESTER RING-OPENED OLIGOMERS AND METHODS OF PREPARATION

BACKGROUND OF THE INVENTION

The invention relates to water soluble and dispersible oligomers, and efficient methods to prepare these new oligomers.

Water soluble and dispersible polymers are in great demand for use as surfactants. Low molecular weight amphiphilic compounds can also be used as surfactants. For example, fatty acid esters of carbohydrates are useful as surfactants. The incorporation of carbohydrates into water soluble and dispersible polymers is thus a promising strategy for the design of new amphiphilic compounds.

There are some potential difficulties in the conversion of carbohydrate building blocks into oligomers and polymers. Carbohydrates contain multiple hydroxyl groups; some of these groups have similar reactivities, making regioselective reactions difficult to achieve. Chemical methods involving multiple protection/deprotection steps for the regioselective esterification of carbohydrates and their derivatives have been studied. The protection/deprotection steps can be eliminated with the use of biological catalysts, such as enzymes. Specific enzymes which include lipases and proteases have been successfully used for the regioselective esterification of the primary hydroxyl groups of various carbohydrates in polar aprotic solvents.

For example, Therisod et al., *J. Am. Chem. Soc.* 108:5638 (1986), reported the regioselective esterification of various carbohydrates, using porcine pancreatic lipase (PPL) as the enzyme and pyridine as the solvent. Riva et al., *J. Am. Chem. Soc.* 110:584 (1988), disclosed the PPL-catalyzed regioselective esterification of carbohydrates in dimethyl formamide (DMF). In addition, Adelhorst et al., *Synthesis* 112 (1990), described regioselective esterifications in the absence of solvent; they reported the solvent-free esterification of ethylglucoside with fatty acids using *Candida antarctica* lipase as the catalyst.

SUMMARY OF THE INVENTION

The invention is based on the discovery that the enzyme-catalyzed reaction of carbohydrates and cyclic monomers, such as lactones and cyclic carbonates, produces novel oligomers. The oligomers include a carbohydrate head group and an oligomer chain, which is linked to a primary hydroxyl group of the carbohydrate head group. The oligomer chain can be an oligo-ester chain, an oligo-carbonate chain, or an oligomer that includes both ester and carbonate linkages. The invention is further based on the discovery that the addition of water to enzyme-catalyzed oligomerizations of cyclic esters, such as lactones and cyclic carbonates, increases the reaction rate.

In one aspect, the invention features an oligomer that includes an oligomer chain and a carbohydrate head group that has a primary hydroxyl group; the oligomer chain is linked to the primary hydroxyl group. The oligomer can contain one carbohydrate head group and one oligomer chain; alternatively, the oligomer can contain more than one oligomer chain, each linked to a primary hydroxyl group of the carbohydrate head group.

The carbohydrate head group can have from 1 to about 10 sugar units and can include an anomeric carbon that is linked to an alkoxy group having from 1 to about 10 carbon atoms. An example of such a carbohydrate head group is ethylglucopyranoside. In one embodiment, only the 6 -position of the ethylglucopyranoside is linked to an oligomer chain.

The oligomer chain can be an oligo-ester chain formed from the ring-opening polymerization of one lactone or the ring-opening co-polymerization of at least two lactones. Examples of lactones include ω-pentadecalactone, ω-dodecalactone, δ-valerolactone, lactide, glyocolide, β-methyl-β-propiolactone, α-methyl-β-propiolactone, ε-caprolactone, and γ-butyrolactone.

Alternatively, the oligomer chain can be an oligocarbonate chain formed from the ring-opening polymerization of one cyclic carbonate or the ring-opening copolymerization of at least two cyclic carbonates. Examples of cyclic carbonates include trimethylene carbonate, tetramethylene carbonate, and 2,2-dimethyl trimethylene carbonate.

In another aspect, the oligomer chain can be an oligo-ester/carbonate chain formed from the ring-opening copolymerization of a lactone and a cyclic carbonate.

The invention also features a process for making an oligomer. The process includes mixing a carbohydrate, an enzyme, and a cyclic monomer, such as a lactone or a carbonate, under conditions and for a time sufficient to generate an oligomer. The resulting oligomer includes an oligomer chain linked to a primary hydroxyl group of the carbohydrate. Examples of enzymes include porcine pancreatic lipase and *Candida antarctica* lipase. The invention also features oligomers prepared by this method.

In another aspect, the invention features a process for increasing the ring-opening polymerization rate of a cyclic monomer. The process includes combining the cyclic monomer, such as a lactone or a cyclic carbonate, the enzyme, and an amount of water, under conditions and for a time sufficient to generate an oligomer. The ring-opening polymerization rate is increased by at least 20% when the amount of water is increased from about 0.20% to about 5.6%.

"Primary hydroxyl group," as used herein, means a hydroxyl group bound to a carbon atom that has two hydrogen atoms bound to it.

"Secondary hydroxyl group," as used herein, means a hydroxyl group bound to a carbon that has one hydrogen atom bound to it.

"Carbohydrate head group," as used herein, means a carbohydrate in which at least one of the primary hydroxyl groups is linked to an end of an oligomer chain.

As referred to herein, the positions of the carbohydrate head groups are numbered according to conventional numbering schemes for carbohydrates, as described in McMurry, *Organic Chemistry,* Brooks/Cole: Monterey, p. 883 (1984).

"Oligomer chain," as used herein, means a series of ester or carbonate moieties linked together by covalent bonds; the chain can contain from 2 to 100 moieties, e.g., 6, 10, 25, 50, or 75 moieties.

"Oligo-ester chain," as used herein, means a series of ester moieties in which the carbonyl of an ester moiety is linked by a covalent bond to the non-carbonyl oxygen of another ester moiety; the chain can contain from 2 to 100 ester moieties, e.g., 6, 10, 25, 50, or 75 moieties.

"Oligo-carbonate chain," as used herein, means a series of carbonate moieties in which the carbonyl of a carbonate moiety is linked by a covalent bond to a non-carbonyl oxygen of another carbonate moiety; the chain can contain from 2 to 100 carbonate moieties, e.g., 6, 10, 25, 50, or 75 moieties.

"Oligo-ester/carbonate chain" as used herein, means a series of ester and carbonate moieties in which the carbonyl of one ester or carbonate moiety is linked by a covalent bond to a non-carbonyl oxygen of another ester or carbonate moiety. The chain can contain from 2 to 100 ester or carbonate moieties, e.g., 6, 10, 25, 50, or 75 moieties.

"Sugar unit," as used herein, means a five or six-membered ring sugar. A single sugar unit is also known as a monosaccharide. The units can be linked to other sugar units. For example, a molecule containing two sugar units is also known as a disaccharide.

The new oligomers and methods for preparing them offer several advantages. The oligomers are amphiphilic; i.e., they have a carbohydrate head group which is hydrophilic and an oligo-ester, oligo-carbonate, or oligo-ester/carbonate chain which is hydrophobic. This property makes the oligomers useful as surfactants. In addition, the carbohydrate head groups have well-defined spatial geometries. The strict control of the product spatial geometry enabled by the new methods allows surface activity to be optimized. Furthermore, the carbohydrate head groups contain free hydroxyl groups, which can be further modified to control the hydrophobic/hydrophilic balance of the oligomers, or to prepare block copolymers.

Since the reactions are enzyme-catalyzed, there is no need for tedious protection/deprotection steps to differentiate between the different hydroxyl groups of the carbohydrate head groups; the process is therefore relatively efficient. The oligomers can also be prepared in bulk reactions; this eliminates the need for solvents such as dimethyl formamide (DMF) and pyridine, which can cause low yields and solvent toxicity. Bulk reactions also increase product yield in relation to reaction volume, thus decreasing production costs.

The methods for preparing oligo-esters, oligo-carbonates, and oligo-ester/carbonates in the presence of controlled quantities of water offer the advantage of relatively fast reaction rates.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based on the discovery that the enzyme-catalyzed reaction of carbohydrates and cyclic monomers, such as lactones and cyclic carbonates, produces novel oligomers. The oligomers include a carbohydrate head group and an oligomer chain, which is linked to a primary hydroxyl group of the carbohydrate head group. The oligomer chain can be an oligo-ester chain, an oligo-carbonate chain, or an oligo-ester/carbonate chain. The invention is further based on the discovery that the addition of water to enzyme-catalyzed oligomerizations of cyclic esters such as lactones and cyclic carbonates increases the reaction rate.

Preparation of Starting Materials

Carbohydrates used in the present invention can be purchased from Aldrich Chemical Company, Wisconsin, or prepared according to the methods described in Adelhorst et al., supra. The carbohydrates can be used as a mixture of α- and β-anomers. Furthermore, the carbohydrates can be monosaccharides, disaccharides, or higher chain length oligosides. These carbohydrates can be linked at the anomeric carbon to an alkoxy group such as methoxy or ethoxy.

Examples of carbohydrates include alkylpyranoside derivatives of mono-, di-, and oligosaccharides such as glucose, mannose, galactose, fructose, lactose, cellobiose, methylglucopyranoside, ethylglucopyranoside, ethylcellobiose, ethylfructose, butylglucopyranoside, and methylgalactopyranoside. A useful carbohydrate is ethylglucopyranoside.

Lactones used in the present invention can be purchased from Aldrich Chemical Company, Wisconsin, or prepared according to the methods described in Johns et al., *Ring-opening Polymerization*, Elsevier: New York, Vol. 1, p. 461 (1984). Examples of lactones include ω-pentadecalactone, ω-dodecalactone, δ-valerolactone, lactide, glyocolide, β-propiolactones (e.g., β-methyl-β-propiolactone or α-methyl-β-propiolactone), ε-caprolactone, and γ-butyrolactone. A useful lactone is ε-caprolactone. The lactones can be distilled over a drying agent, e.g., CaH$_2$, under reduced pressure prior to the reaction.

Cyclic carbonates used in the present invention can be purchased from Aldrich Chemical Company, Wisconsin, or prepared according to the methods described in Ariga et al., *J. Polym. Sci.*, 31:581 (1993). Examples of cyclic carbonates include trimethylene carbonate, tetramethylene carbonate, and 2,2-dimethyl trimethylene carbonate. A useful carbonate is trimethylene carbonate. The carbonates can be distilled over a drying agent, e.g., CaH$_2$, under reduced pressure prior to the reaction.

Enzymes used in the present invention can be purchased from Sigma Chemical Company, Missouri; Amano Enzyme USA Company, Ltd., Illinois; and Novo Nordisk Bioindustrials, Inc., North Carolina, and used without further purification. Alternatively, the enzymes can be purified according to the methods described in Jakoby, W. B., ed., *Enzyme Purification and Related Technicues,* Academic Press: New York, Vol. 22 (1972). Examples of enzymes include lipases from *Aspergillus niger, Candida cylindracea, Candida rugosa, Rhizopus delmar, Rhizopus javanicus, Pseudomonas fluorescens,* Pseudomonas sp., *Candida antarctica* (available under the trade name NOVOZYME 435™, from Novo Nordisk Bioindustrials, Inc., North Carolina), phospholipase, and porcine pancreatic lipase. A useful enzyme is porcine pancreatic lipase. The enzyme can be dried in a vacuum desiccator under reduced pressure prior to the reaction. The enzymes can be used crude, purified, immobilized on supports such as CELITE® (available from Aldrich Chemical Company, Wisconsin), or activated by surfactant-enzyme interactions.

Synthesis of Carbohydrate-Ester Oligomers

The enzyme-catalyzed ring-opening of cyclic esters such as lactones and cyclic carbonates by carbohydrates can be carried out as follows. Using a glove bag and dry argon to maintain an inert atmosphere, the carbohydrate and the enzyme are transferred to an oven-dried reaction vial. The ratio (w/w) of carbohydrate to enzyme is 100:1 to 0.5:1, e.g., 1:1. The vial is immediately stoppered with a rubber septa and purged with argon. The cyclic ester is added via syringe under argon. The ratio (w/w) of cyclic ester, relative to the lipase added, is 1:1 to 40:1, e.g., 2:1, 7:1, or 20:1. The reaction vial is then placed in a constant temperature oil bath maintained at anywhere from 25 to 100° C., e.g., 40° C. or 75° C., for anywhere from 1 to 160 hours, e.g., 80 or 110 hours.

The reaction is monitored by thin-layer chromatography until more than 80%, e.g., more than 95%, of the cyclic ester is consumed. The reaction is quenched by removing the enzyme by vacuum filtration (glass fritted filter, medium-pore porosity). The enzyme is washed 3–4 times with 1 to 20 mL, e.g., 3 to 7 mL, portions of a solvent, e.g., chloroform, and the filtrates are combined. The solvent is removed in vacuo to yield product.

The product can be purified by column chromatography over silica gel (e.g., 130–270 mesh, 60 Å) using a gradient solvent system of nonpolar and polar organic solvent (1 to 10 mL/minute, e.g., 1 to 4 mL/minute).

Oligomerization of Lactones in the Presence of Water

The enzyme-catalyzed ring-opening of cyclic monomers, such as lactones and cyclic carbonates, in the presence of water can be carried out as follows. The cyclic monomer and the lipase are separately dried in reaction vials. The ratio (w/w) of cyclic monomer to lipase can be from 1:1 to 40:1, e.g., from 2.1:1 to 6.7:1. Varying levels of reaction water content are obtained by drying the enzyme. The enzyme can be, for example, (1) used without drying; (2) dried over $P_2O_5$ in a desiccator at reduced pressure; (3) or dried over $P_2O_5$ using a diffusion pump in a drying pistol under reduced pressure and elevated temperature. The contents of the vials are mixed under a dry argon atmosphere in a glove bag and securely capped. The vials are further sealed with Teflon tape and placed in constant temperature oil baths. The reactions are terminated by dissolving the residual monomer and oligomer in organic solvent, e.g., chloroform, and separating the insoluble enzyme by filtration, using fritted glass filters. The insoluble materials are washed with portions of fresh solvent. The filtrates are then combined, and the solvent is removed under reduced pressure at an elevated temperature.

Alternatively, the enzyme can be deactivated by, for example, cooling to room temperature. In this case, the enzyme is not removed from the final product.

The presence of water increases the reaction rates; the more water that is present in the reaction, the faster the reaction rate.

Characterization and Uses for Carbohydrate-Ester Oligomers

Oligomers prepared by the new method contain at least one carbohydrate head group in which a primary hydroxyl group is esterified. The oligomers further contain oligomer chains, e.g., oligo-ester chains, oligo-carbonate chains, or oligo-ester/carbonate chains. The molecular weights of the oligomers can be from about 200 to about 5,000 g/mol.

Due to the presence of free hydroxyls on the carbohydrate head group, there are opportunities for further modification. For example, the product oligomers can be used to prepare block copolymers of lactones and cyclic carbonates. First, the above-described enzyme catalyzed polymerization of a momoner, using one or more primary hydroxyl groups of the carbohydrate head group as initiators, is carried out. Next, stannous octanoate is used to catalyze the polymerization of a second monomer, using one or more of the remaining hydroxyl groups of the carbohydrate head group as initiators.

Alternatively, the hydrophobic/hydrophilic balance of the product oligomers can be tailored by elaboration of the free hydroxyl groups to provide charged groups, such as carboxylate groups. This can be accomplished by the addition of compounds such as succinic anhydride, 3,3-dimethyl glutaric anhydride, or citraconic anhydride.

The new oligomers of the present invention are useful as biodegradable surfactants for applications in detergents and cosmetic formulations. For example, oligomers prepared using the carbohydrate ethylglucopyranoside and the lactone ε-caprolactone are useful as biodegradable surfactants that are useful in creating oil-in-water dispersions.

The oligomers can also be used as interfacial agents for biodegradable blends. For example, multi-arm oligomers can be prepared by reacting ethylglucose-oligo(ε-caprolactone) with lactide using stannous octanoate as the catalyst. The multi-arm oligomers are useful compatibilizers for blends of poly(ε-caprolactone) and poly(lactide).

In addition, the oligomers can also be used to form biocompatible micelles. For example, oligomers prepared using the carbohydrate butylcellobiose and the lactone lactide can form micelles with hydrophobic interiors and hydrophilic exteriors. These micelles can be used for the controlled release of hydrophobic low molecular weight drugs. The drugs are initially contained in the hydrophobic interior of the micelle, then slowly diffuse out of the micelles in vivo.

The invention is further described in the following examples, which do not limit the scope of the claimed invention.

EXAMPLES

Example 1
Preparation of Oligo(ε-CL)-EGP

The enzyme-catalyzed ring-opening of ε-caprolactone (ε-CL) by ethylglucopyranoside (EGP) was carried out as follows. Using a glove bag and dry argon to maintain an inert atmosphere, 200 mg of EGP and 500 mg of porcine pancreatic lipase were transferred to an oven-dried 20 mL reaction vial. The vial was immediately stoppered with a rubber septa and purged with argon. 0.8 mL of ε-CL was added via syringe under argon. The reaction vial was then placed in a constant temperature oil bath maintained at 70° C. for 96 hours. A control reaction was set up as described above, except that PPL was not added.

In the reaction vial, more than 95% of the EGP (determined by thin-layer chromatography) was consumed in 96 hours. The reaction was quenched by removing the enzyme by vacuum filtration (glass fritted filter, medium-pore porosity). The enzyme was washed 3–4 times with 5 mL portions of chloroform, and the filtrates were combined. The solvent was removed in vacuo to give 950 mg of oligo(ε-CL)-EGP.

The product (500 mg) was purified by column chromatography over silica gel (10 g, 130–270 mesh, 60 Å) using a gradient solvent system of hexane-ethyl acetate (2 mL/minute) with an increasing order of polarity, to yield 450 mg of purified oligo(ε-CL)-EGP.

Example 2

Analysis of Oligo(ε-CL)-EGP

The molecular weight of the oligo(ε-CL)-EGP made in Example 1 was determined by gel permeation chromatography (GPC), performed on a Waters Corporation, Massachusetts, model 510 pump equipped with a model 410 refractive index detector, a model 486 UV detector and a model 717 autosampler with 500, $10^3$, $10^4$, and $10^5$ Å ULTRASTRYRAGEL® columns (available from Waters) in series. Chloroform (HPLC grade) was used as the eluent at a flow rate of 1.0 ml/minute. The sample concentration and injection volumes were 0.3% (w/v) and 100 μL, respectively. The molecular weights were calculated based on comparison to polystyrene standards without further correction.

The resulting oligomer had a number average molecular weight ($M_n$) of 2200 g/mol and polydispersity 1.26. The structure of the product was confirmed by proton ($^1$H), carbon ($^{13}$C), DEPT-135 ($^{13}$C) and COSY ($^1$H—$^1$H) nuclear magnetic resonance (NMR) spectra.

$^1$H-NMR spectra were recorded on a Bruker ARX-250 spectrometer at 250 MHz. $^1$H-NMR chemical shifts in parts per million are reported downfield from 0.00 ppm using tetramethylsilane (TMS) as an internal reference. The concentration of substrate used was 4% w/v in dimethylsulfoxide-$d_6$. The instrumental parameters were as follows: temperature 300 K., pulse width 7.8 μs (30°), 32K data points, 3.178-s acquisition time, 1-s relaxation delay, and 16 transients.

The $^1$H NMR spectrum of oligo(ε-CL)-EGP in CDCl$_3$ contained peaks due to oligo(ε-CL) at 4.08(t, J=6.6 Hz), 3.65(t, J=6.6 Hz), 2.38(m), 1.65(m), and 1.39(m) ppm. The $^1$H signals due to the ethylglucoside moiety were found at 4.88(d, J=3.8 Hz), 4.45–4.25(m), 3.94–3.30(m) and 1.25(t, J=7.5 Hz) ppm. This spectrum, due to poorly resolved signals, was not useful in determining the position at which oligo(ε-CL) was linked to the carbohydrate head group.

$^{13}$C-NMR spectra were recorded at 62.9 and 125 MHz on Bruker ARX-250 and ARX-500 spectrometers, respectively, with chemical shifts in ppm referenced relative to DMSO-$d_6$ as the internal reference at 39.7 ppm. For comparison, $^{13}$C NMR spectra of oligo(ε-CL)-EGP and oligo(ε-CL) were also recorded in CDCl$_3$. Spectral acquisitions were conducted as 10% w/v DMSO-$d_6$ or CDCl$_3$ solutions using the following parameters: 300 K, pulse width 6.3 μs (30°), 64K data points, 1.638-s acquisition time, 1-s relaxation delay, and 15000–18000 transients.

Figure 1A:
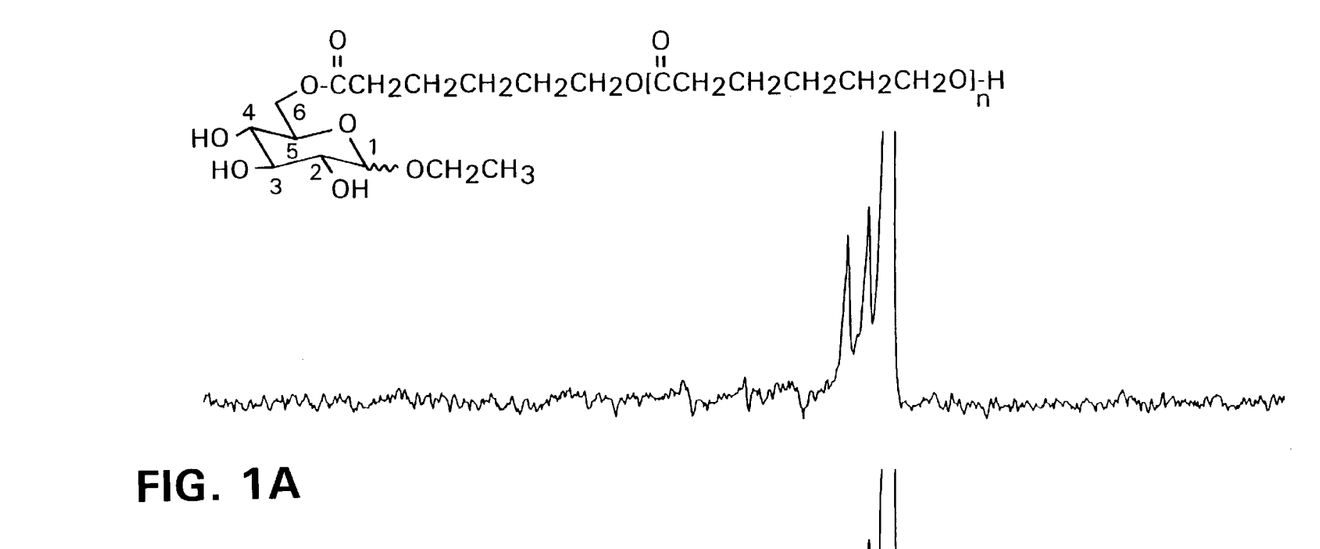
FIGS. 1A and 1B are regions of $^{13}$C-NMR spectra of an oligomer prepared with ε-caprolactone and ethylglucopyranoside showing the peaks associated with (A) the product oligomer with a free hydroxyl group, and (B) the oligomer, derivatized with diazomethane, showing that initiation of chains by water was negligible.
Figure 2A:
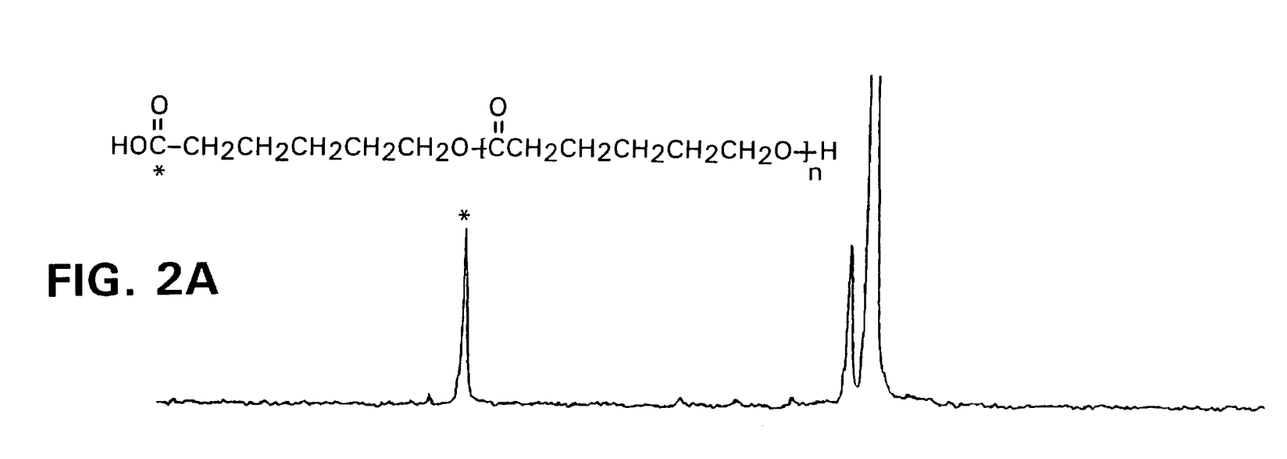
FIGS. 2A and 2B are regions of $^{13}$C-NMR spectra of an oligomer prepared from ε-caprolactone without ethylglucopyranoside showing the peaks associated with (A) the product oligomer with a free hydroxyl group, and (B) the oligomer, derivatized with diazomethane, showing the presence of carboxyl terminal chain ends.
Figure 2B:
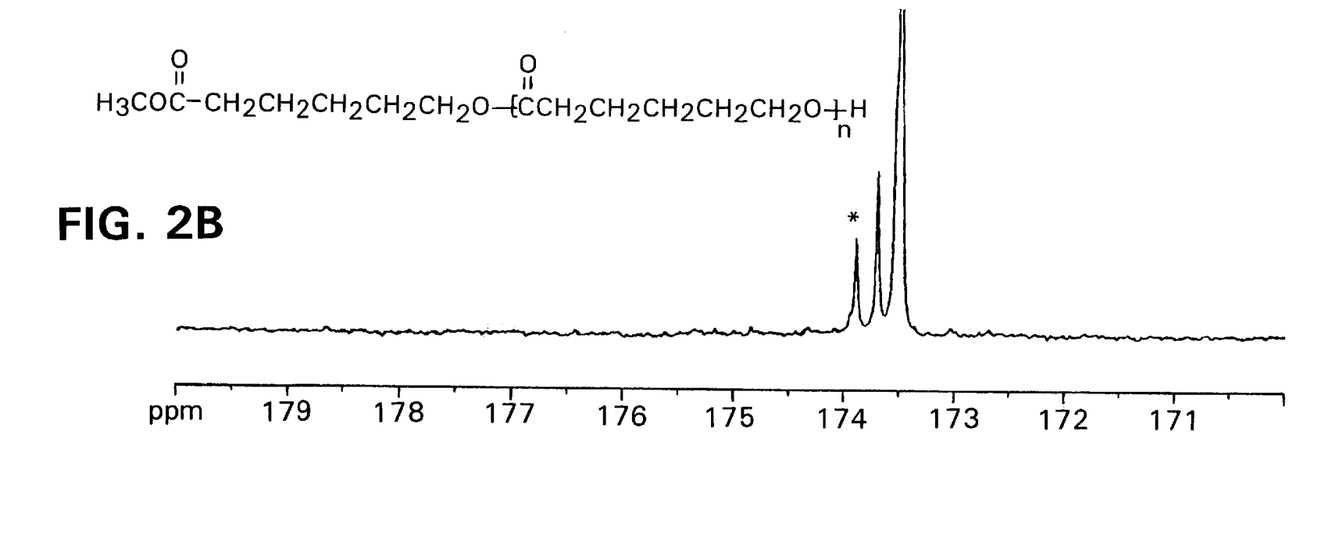

The $^{13}$C-NMR spectrum of oligo(ε-CL)-EGP had signals due to carbonyl carbons at 174.0, 173.8, and 173.6 ppm (FIG. 1A). If a fraction of the oligo(ε-CL) chains were initiated by water, this would result in carboxyl terminal chain ends. Oligo(ε-CL), having chain-end carboxyl functional groups, was prepared by PPL catalyzed ring-opening polymerization of ε-CL. The chain-end carboxyl groups were esterified with diazomethane, and its $^{13}$C-NMR spectrum (FIG. 2B) was compared with that of the un-esterified product (FIG. 2A). The signal (marked by an asterisk) observed for the oligo(ε-CL) at 177.2 ppm (due to carboxylic acid end groups) was shifted upfield by about 3 ppm, to 173.9 ppm, in the esterified product (FIG. 2B).

Figure 1B:
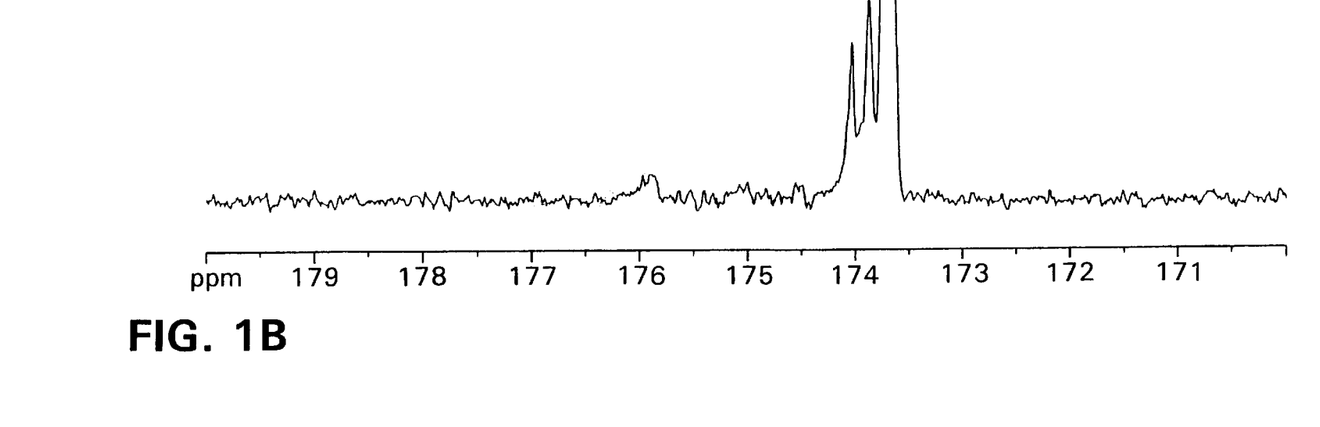

Therefore, the fact that there was no notable difference between the spectra shown in FIG. 1A and FIG. 1B is evidence that initiation of chains by water was negligible, as there were no carboxyl terminal chain ends.

Figure 3:
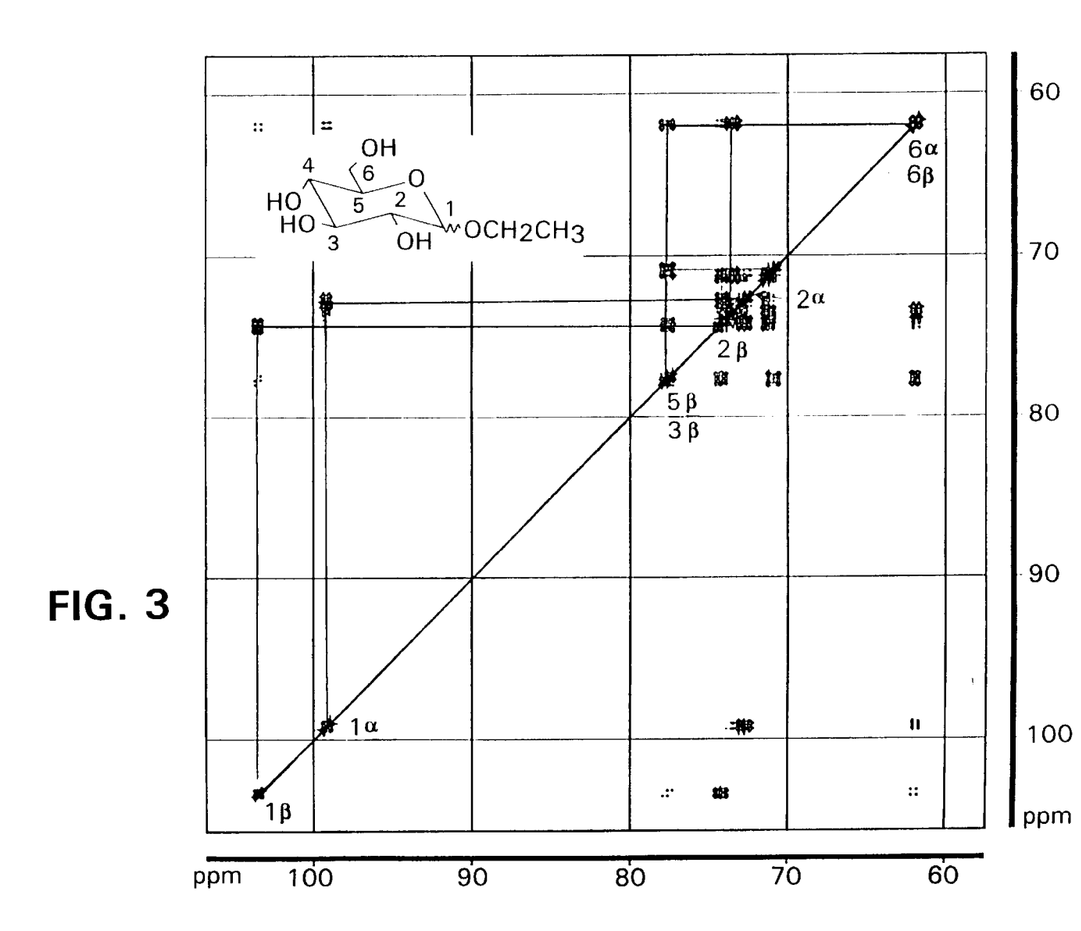
FIGS. 3 and 4 are $^{13}$C—$^{13}$C COSY spectra of $^{13}$C$_6$-ethylglucoside showing the carbon peaks due to the α- and β-anomers.
Figure 4:
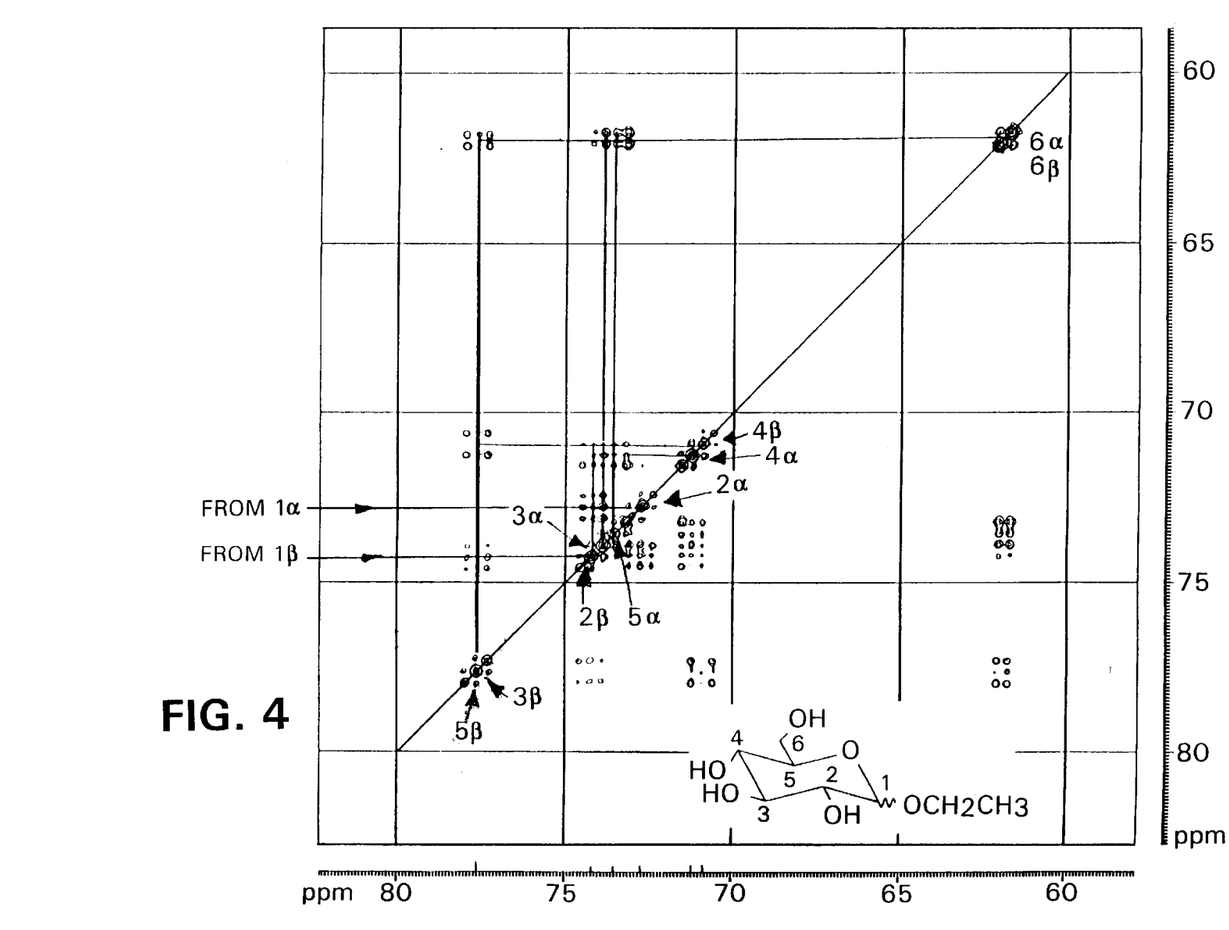

The literature describing NMR characterization of ethylglucose does not provide a suitable basis for assignment of the $^{13}$C-NMR signals. Therefore, the assignment of signals in the $^{13}$C-NMR spectrum of EGP was confirmed with the help of a $^{13}$C—$^{13}$C COSY experiment on $^{13}$C$_6$-EGP. Analysis of $^{13}$C$_6$-EGP by $^{13}$C—$^{13}$C COSY NMR showed cross peaks between signals due to the β-anomer at 103.4 (β C-1) and 74.3 (β C-2) ppm; 74.3 (β C-2) and 77.6 (β C-3) ppm; 77.6 (β C-3) and 71.0 (β C-4) ppm; 71.0 (β C-4) and 77.6 (βC-5); and 77.6 (β C-5) and 62.0 (β C-6) ppm. In addition, crosspeaks between signals of the α-anomer at 99.2 (α C-1) and 72.8(α C-2); 72.8 (α C-2) and 74.2 (α C-3); 74.2 (α C-3) and 71.3 (α C-4); 71.3 (α C-4) and 173.5 (α C-5); and 73.5 (α C-5) and 61.9 (α C-6) ppm were seen (FIGS. 3 and 4).

DEPT-135 spectra were recorded at 62.9 MHz on a Bruker ARX-250 spectrometer as 10% DMSO-$d_6$ solutions at 300K, 64 K data points, 1.638-s acquisition time, 1-s relaxation delay and 10000–15000 transients. For the ($^1$H—$^1$H) COSY experiment (4% w/v product in DMSO-$d_6$) the data were collected in a 1024×128 data matrix and zero filled to 512×512 using 8 scans per increment, a 1915 Hz sweep width, and 1.93-s delay between transients.

Figures 5A, 5B:
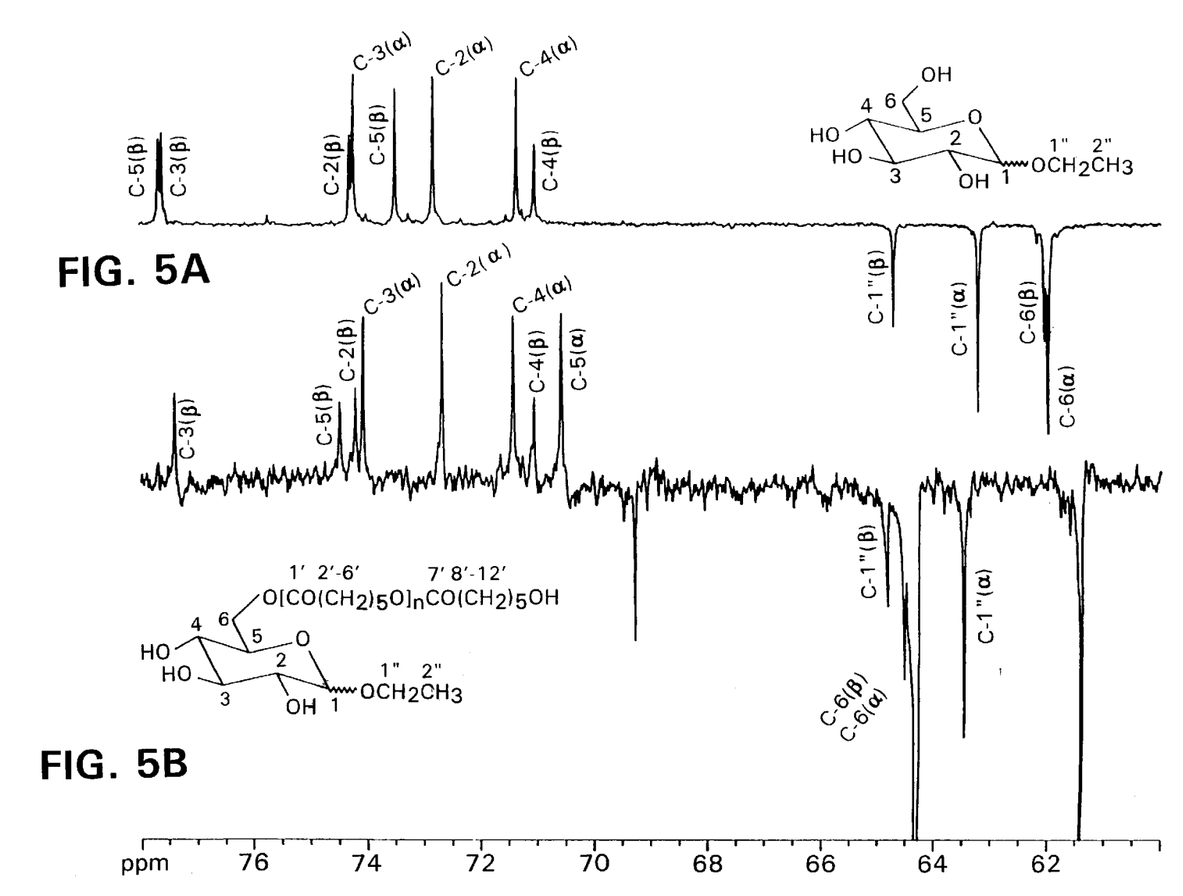
FIGS. 5A and 5B are partial DEPT-135 spectra of (A) ethylglucoside and (B) the product oligomer, showing that the C-6 primary hydroxyl position of ethylglucopyranoside served as the site for initiation of the ε-CL oligomerization.
Figure 6:
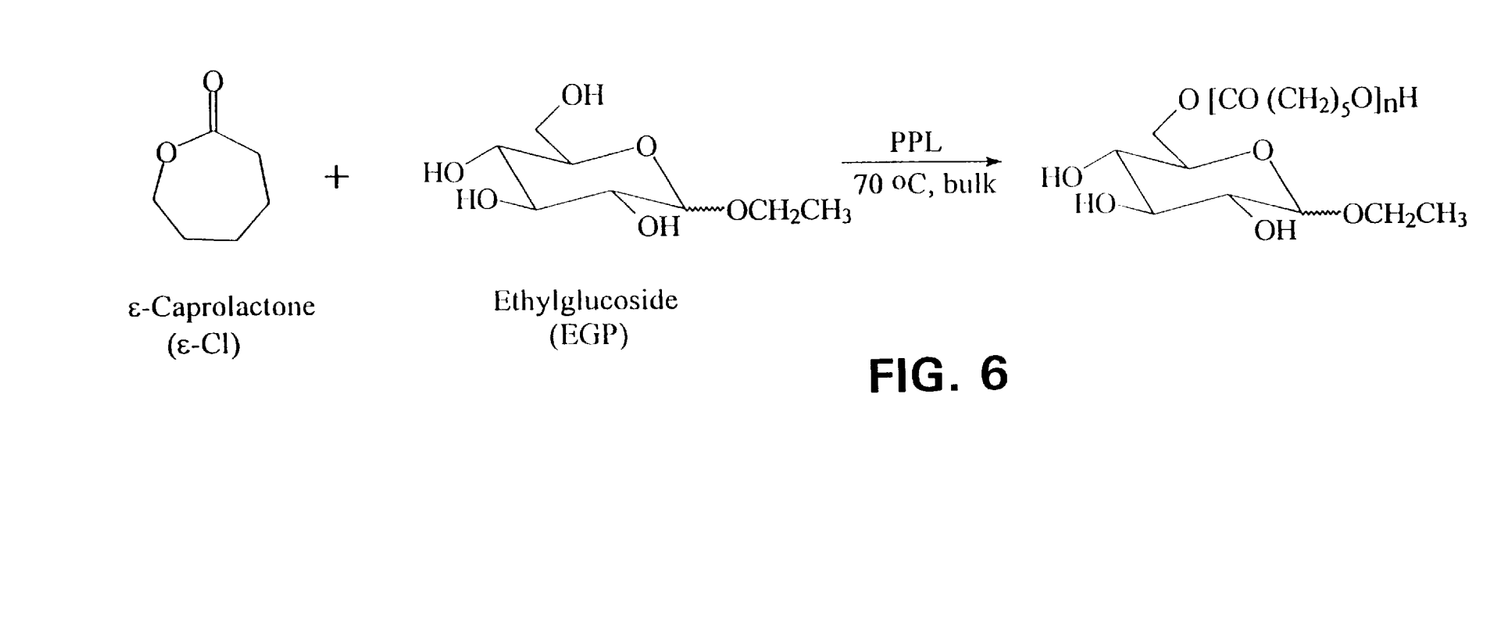
FIG. 6 is a schematic representation of the reaction of ε-caprolactone and ethylglucopyranoside to form an oligomer.

A DEPT-135 spectrum of EGP gave additional evidence that the C-6 signals were at 61.9 (α) and 62.0 (β) ppm (FIG. 5A). A comparison of the DEPT-135 spectra of EGP with that of the product from ε-CL ring-opening showed a downfield shift of 2.4 ppm for the signals corresponding to the EGP C-6 α- and β- anomers (FIG. 5B). Furthermore, signals originally observed at 61.9 and 62.0 ppm were no longer detected in the product (FIG. 5B). These results indicate that the C-6 primary hydroxyl position of EGP served as the site for initiation of ε-CL polymerization. The result is an oligomer in which only the 6-position of EGP is linked to the oligo-ester chain, as shown in FIG. 6.

This conclusion was supported by an upfield shift of 3.0 ppm in the resonance position of EGP C-5 subsequent to ε-CL polymerization, due to the γ-effect. Moreover, all other carbon resonances assigned to EGP showed no substantial change in chemical shift subsequent to ε-CL polymerization. This data provides further support for the conclusion that regioselective ring-opening oligomerization of ε-CL using EGP as a multifunctional initiator was achieved.

In addition, it is noteworthy that there was no observed preference for reaction with ε-CL by either the EGP α- or β-anomer. Thus, both anomers are useful as initiators to form oligo(ε-CL)-EGP products.

Figure 7:
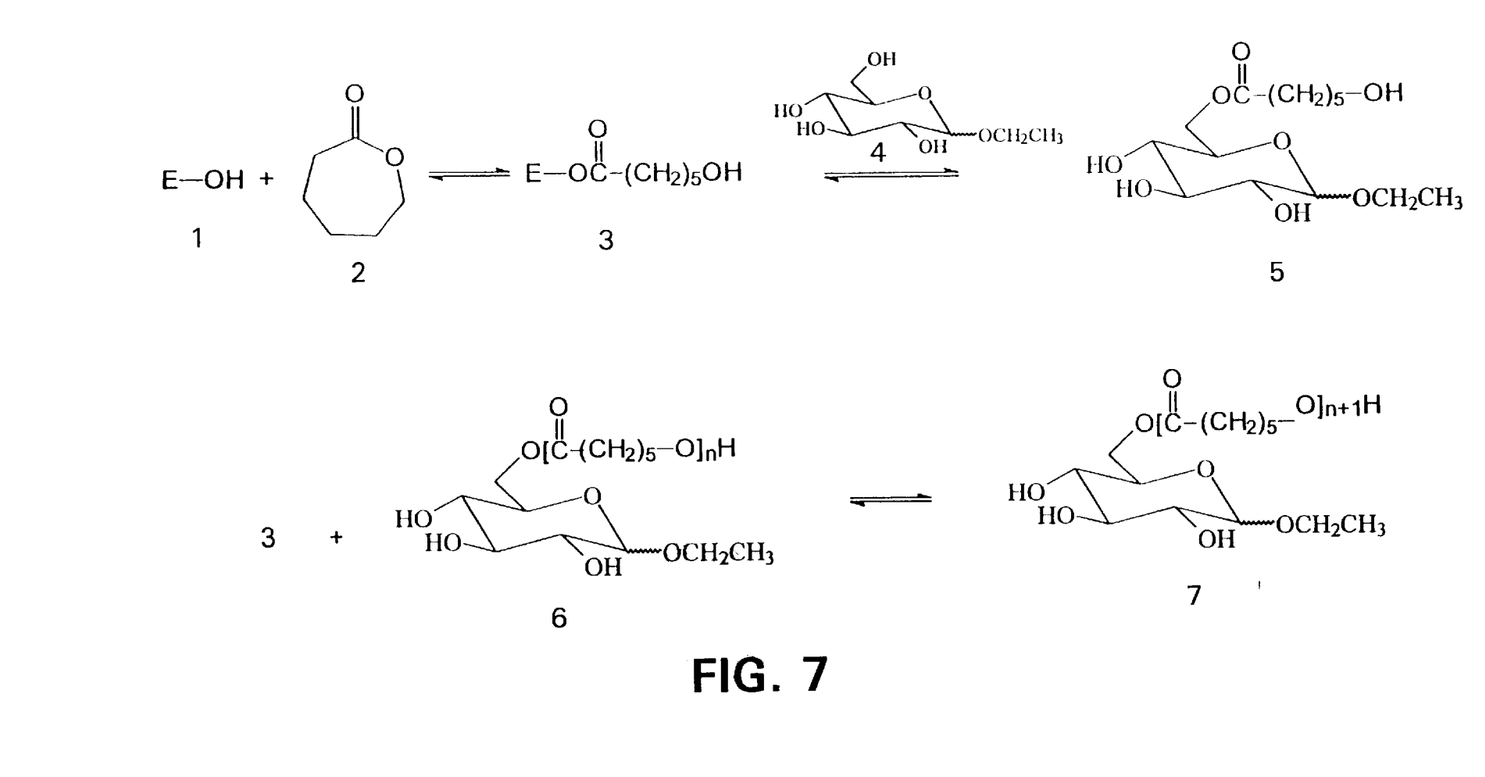
FIG. 7 is a schematic representation of the proposed mechanism of the reaction of porcine pancreatic lipase, ε-caprolactone, and ethylglucopyranoside.

Based upon the structure of the oligo-lactone-carbohydrate product, it is believed that the formation of the oligomers occurs as shown schematically in FIG. 7. The enzyme 1 first reacts with the ε-caprolactone 2 forming an enzyme-activated monomer (EAM) complex 3 in which the lactone has been opened. Initiation of the oligo(ε-CL) chain occurs by reaction of ethylglucopyranoside 4 with the EAM complex 3 to form the esterified ethylglucopyranoside 5. As shown in FIG. 7, only the 6-position of the ethylglucopyranoside 4 reacts with the EAM complex 3. Propagation of the oligo(ε-CL) chain then occurs by reaction of either 5 or 6 with the EAM complex 3, resulting in an oligomer 7 with a ethylglucopyranoside head group and an oligo(ε-CL) chain.

Example 3

Preparation of oligo(ε-CL)-EGP catalyzed by *Candida antarctica* lipase

The enzyme-catalyzed ring-opening of ε-CL by EGP was carried out as follows. Using a glove bag and dry argon to maintain an inert atmosphere, 200 mg of EGP and 500 mg of *Candida antarctica* lipase (available under the trade name NOVOZYME 435™, from Novo Nordisk Bioindustrials, North Carolina) were transferred to an oven-dried 20 mL reaction vial. The vial was immediately stoppered with a rubber septum and purged with argon. 0.8 mL of ε-CL was added via syringe under argon. The reaction vial was then placed in a constant temperature oil bath maintained at 70° C. for 96 hours. A control reaction was set-up as described above, except that the enzyme was not added.

The reaction was quenched by removing the enzyme by vacuum filtration (glass fritted filter, medium-pore porosity). The enzyme was washed 3–4 times with 5 mL portions of chloroform, and the filtrates were combined. The solvent was removed in vacuo to give 960 mg of oligo(ε-CL)-EGP.

The product (500 mg) was purified by column chromatography over silica gel (10 g, 130–270 mesh, 60 Å) using a gradient solvent system of hexane-ethyl acetate (2 mL/minute) with an increasing order of polarity, to yield 450 mg of purified oligo(ε-CL)-EGP.

Example 4

Characterization of oligo(ε-CL)-EGP

The regiospecificity of the oligo(ε-CL)-EGP product was determined by NMR experiments, as described above for oligo(ε-CL)-EGP formed using PPL as the catalyst.

A (ε-CL)-EGP fraction of the product from *Candida antarctica* lipase catalysis of low molecular weight ((ε-CL)-EGP monoadduct) was isolated by column chromatography (silica gel, 15% EtOH/CHCl$_3$). The DEPT-135 NMR spectrum (CDCl$_3$) of this mono(ε-CL)-gEGP product was compared with that of oligo(ε-CL)-EGP from PPL catalysis (described in Examples 1 and 2). The chemical shift positions of EGP carbon signals C-1 to C-6 were identical for these two products. These results confirmed that *Candida antarctica* lipase was as effective as PPL in catalyzing the regioselective reaction of EGP primary hydroxyl groups with ε-CL to form well defined ring-opened products.

The molecular weight of the oligo(ε-CL)-EGP product from *Candida antarctica* lipase catalysis was measured by gel permeation chromatography (GPC) as described above for oligo(ε-CL)-EGP formed from PPL catalysis. The number average molecular weight ($M_n$) was 2,500 g/mol.

Example 5

Preparation of oligo(TMC)-EGP catalyzed by *Candida antarctica* lipase

The enzyme-catalyzed ring-opening oligomerization of trimethylene carbonate (TMC) initiated by EGP was carried out as follows. Using a glove bag and dry argon to maintain an inert atmosphere, 200 mg of EGP and 714 mg of TMC were transferred to an oven-dried 20 mL reaction vial. The vial was immediately stoppered with a rubber septum and purged with argon. 500 mg of *Candida antarctica* lipase (available under the trade name NOVOZYME 435™, from Novo Nordisk Bioindustrials, Inc., North Carolina) was then added to the same reaction vial under argon in the glove bag. The reaction vial was placed in a constant temperature oil bath maintained at 70° C. for 96 hours. A control reaction was set-up as described above, except that the enzyme was not added.

The reaction was quenched by removing the enzyme by vacuum filtration (glass fritted filter, medium-pore porosity). The enzyme was washed 3–4 times with 5 mL portions of chloroform, and the filtrates were combined. The solvent was removed in vacuo to give 850 mg of oligo(TMC)-EGP.

Example 6

Characterization of oligo(TMC)-EGP

The regiospecificity of the oligo(TMC)-EGP product of Example 5 was determined by NMR experiments, as described above for oligo(ε-CL)-EGP formed from PPL catalysis.

A (TMC)-EGP fraction of the product from *Candida antarctica* lipase (available under the trade name NOVOZYME 435™, from Novo Nordisk Bioindustrials, Inc., North Carolina) catalysis of low molecular weight (TMC-EGP monoadduct) was isolated by column chromatography (silica gel, 15% EtOH/CHCl$_3$). The DEPT-135 NMR spectrum of this mono(TMC)-EGP product was then compared with that of oligo(ε-CL)-EGP from PPL catalysis. The chemical shift positions of EGP carbon signals C1 to C5 were identical for these two products. Also, the carbon signal assigned to C6 or mono(TMC)-EGP was 1 ppm further downfield than C6 of oligo(ε-CL)-EGP. This shift was expected, since the carbonate linkage is more electron withdrawing than the corresponding ester linkage. These results confirmed that *Candida antarctica* lipase catalyzed the regioselective reaction of EGP primary hydroxyl groups with TMC to form well defined ring-opened products.

The molecular weight of oligo(TMC)-EGP was measured by gel permeation chromatography(GPC) as was described above for oligo(ε-CL)-EGP formed from PPL catalysis. The number average molecular weight ($M_n$) of this product was 7200 g/mol, $M_w/M_n$=2.5.

Example 7

Effect of Water Content on Reaction Rates

All reactions were carried out in bulk. ω-pentadecalactone (PDL, 200 mg) and Pseudomonas sp. lipase (PS-30, 50 mg) were separately dried in 6 mL reaction vials. In all cases, the lactone was dried over P$_2$O$_5$ in a desiccator (0.1 mm Hg, 38 hours, room temperature). Three levels of reaction water content were obtained by drying the enzyme using one of the following methods: (1) the enzyme was used without drying; (2) the enzyme was dried over P$_2$O$_5$ in a desiccator (0.1 mm Hg, 38 hours, room temperature); (3) the enzyme was dried over P$_2$O$_5$ using a diffusion pump in a drying pistol (65 μm Hg, 38 hours, 56° C.). Method (1) results in a reaction water content of (wt-% water) 5.60%; method (2) results in a reaction water content of 0.30%; method (3) results in a reaction water content of 0.20%. The contents of the vials were mixed under a dry argon atmosphere in a glove bag and securely capped. The vials were further sealed with Teflon tape and placed in constant temperature oil baths at predetermined reaction temperatures and for predetermined time periods. Control reactions were conducted as above, except that enzyme was not added. The reactions were terminated by dissolving the residual monomer and oligomer in chloroform and separating the insoluble enzyme by filtration, using 10–15 μm glass-fritted filters. The insoluble materials were washed 2 to 3 times with 5 mL portions of fresh chloroform. The filtrates were then combined, and the solvent was removed by rotary evaporation at 40° C.

Example 8
Analysis of Water Content

Total reaction water contents (wt-% water) were measured by using a Mettler DL 18 Karl Fischer titrator with Hydranal-Titrant 5 (Fisher Scientific) and Hydranal Solvent (Fisher Scientific). The water content (w/w) in various reaction mixtures was determined by stirring 50 mg of enzyme and 200 mg of lactone in 2.5 mL of anhydrous DMSO for 24 hours in a closed septum vial under argon atmosphere and then analyzing the water content of the supernatant relative to a DMSO control.

Figure 8:
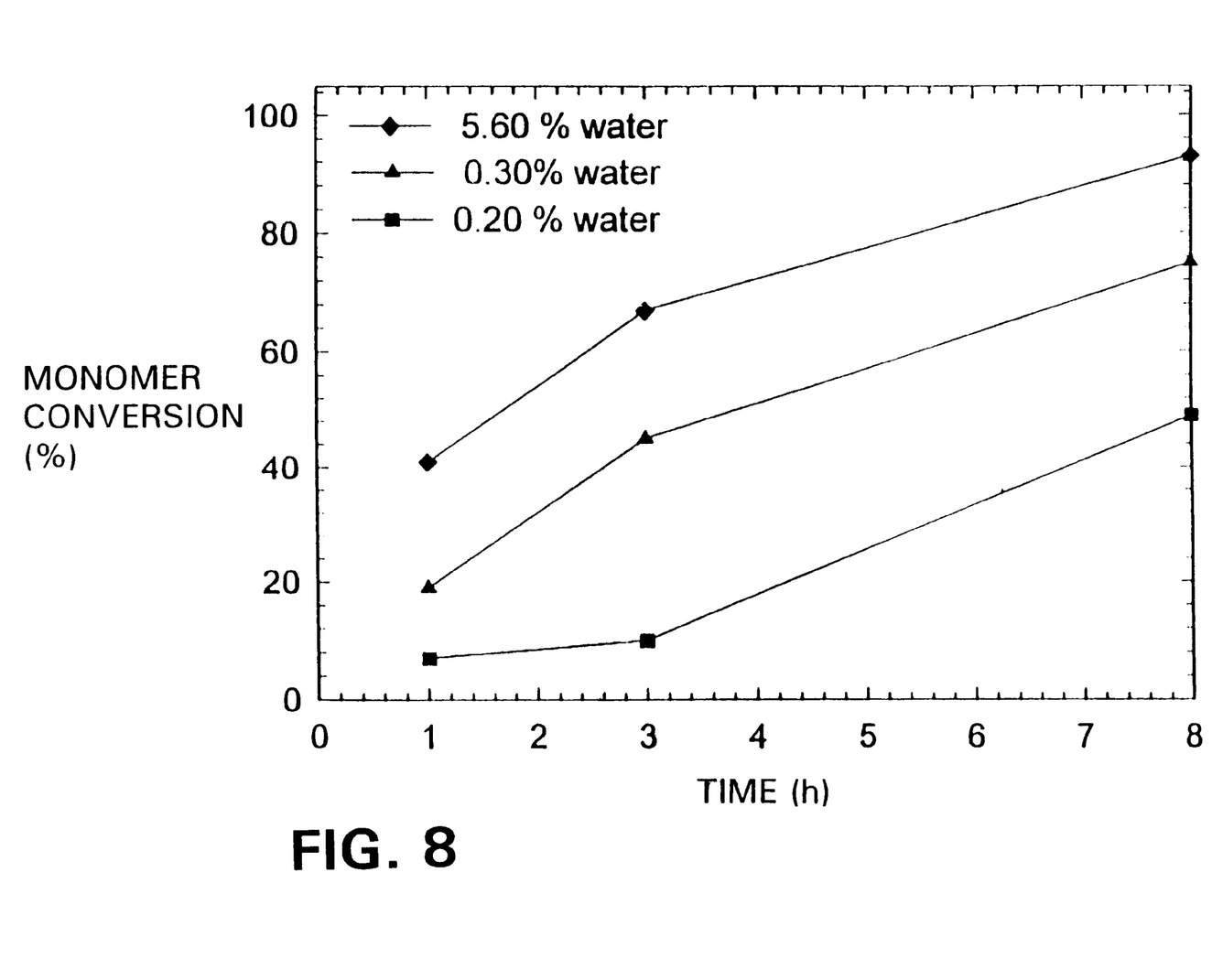
FIG. 8 is a graph showing that an increase in the reaction water content (%-by weight) results in an increase in the rate of monomer conversion for the Pseudomonas sp. lipase (PS-30) catalyzed reactions of ω-pentadecalactone.

The effect of water content on the %-monomer (PDL) conversion for PS-30 catalyzed reactions is shown in FIG. 8. Inspection of the results shows that by increasing the water content in the reactions, enhanced oligomerization rates can be achieved. When the water content is increased from 0.20% to 0.30%, the %-monomer conversion increases from 10% to 43% at a 3 hour reaction time. When the water content is further increased to 5.60%, the %-monomer conversion increases to 67%. Thus, PS-30 activity is enhanced by increasing the shell of enzyme bound water.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An oligomer comprising (a) an oligomer chain and (b) a carbohydrate head group having 1–10 sugar units, at least one of said sugar units comprising a primary hydroxyl group, wherein said oligomer chain is linked to said primary hydroxyl group, and wherein said oligomer chain is an oligo-ester chain, an oligo-carbonate chain, or an oligo-ester/carbonate chain.

2. The oligomer of claim 1, wherein said oligomer consists essentially of one carbohydrate head group and one oligomer chain.

3. The oligomer of claim 1, wherein said carbohydrate head group comprises a second primary hydroxyl group, and wherein said oligomer comprises a second oligomer chain linked to said second primary hydroxyl group.

4. The oligomer of claim 1, wherein said carbohydrate head group comprises an anomeric carbon linked to an alkoxy group comprising from 1 to 10 carbon atoms.

5. The oligomer of claim 4, wherein said carbohydrate head group comprises ethylglucopyranoside.

6. The oligomer of claim 5, wherein only the 6-position of said ethylglucopyranoside is linked to an oligomer chain.

7. The oligomer of claim 1, wherein said oligomer chain comprises an oligo-ester chain formed from the ring-opening polymerization of a lactone.

8. The oligomer of claim 7, wherein said lactone is selected from the group consisting of ω-pentadecalactone, ω-dodecalactone, δ-valerolactone, lactide, glyocolide, β-methyl-β-propiolactone, α-methyl-β-propiolactone, ε-caprolactone, and γ-butyrolactone.

9. The oligomer of claim 8, wherein said lactone is ε-caprolactone.

10. The oligomer of claim 1, wherein said oligomer chain comprises an oligo-ester chain formed from the ring-opening co-polymerization of at least two lactones.

11. The oligomer of claim 10, wherein said lactones are selected from the group consisting of ω-pentadecalactone, ω-dodecalactone, δ-valerolactone, lactide, glyocolide, β-propiolactone, ε-caprolactone, and γ-butyrolactone.

12. The oligomer of claim 1, wherein said oligomer chain comprises an oligo-carbonate chain formed from the ring-opening polymerization of a cyclic carbonate.

13. The oligomer of claim 12, wherein said cyclic carbonate is selected from the group consisting of trimethylene carbonate, tetramethylene carbonate, and 2,2-dimethyl trimethylene carbonate.

14. The oligomer of claim 13, wherein said cyclic carbonate is trimethylene carbonate.

15. The oligomer of claim 1, wherein said oligomer chain comprises an oligo-carbonate chain formed from the ring-opening co-polymerization of at least two cyclic carbonates.

16. The oligomer of claim 15, wherein said cyclic carbonates are selected from the group consisting of trimethylene carbonate, tetramethylene carbonate, and 2,2-dimethyl trimethylene carbonate.

17. The oligomer of claim 1, wherein said oligomer chain comprises an oligo-ester/carbonate chain formed from the ring-opening co-polymerization of a lactone and a cyclic carbonate.

18. The oligomer of claim 17, wherein said lactone is selected from the group consisting of ω-pentadecalactone, ω-dodecalactone, δ-valerolactone, lactide, glyocolide, β-propiolactone, ε-caprolactone, and γ-butyrolactone, and wherein said cyclic carbonate is selected from the group consisting of trimethylene carbonate, tetramethylene carbonate, and 2,2-dimethyl trimethylene carbonate.

19. A process for making the oligomer of claim 1, the process comprising mixing (a) a carbohydrate, (b) an enzyme, and (c) a cyclic monomer selected from the group consisting of lactones and carbonates, under conditions and for a time sufficient to generate an oligomer, said oligomer comprising an oligomer chain linked to a primary hydroxyl group of said carbohydrate.

20. The process of claim 19, wherein said enzyme is porcine pancreatic lipase.

21. The process of claim 19, wherein said enzyme is *Candida antarctica* lipase.

22. The process of claim 19, wherein said carbohydrate comprises from 1 to 10 sugar units.

23. The process of claim 22, wherein said carbohydrate comprises an anomeric carbon linked to an alkoxy group having from 1 to 10 carbon atoms.

24. The process of claim 19, wherein said cyclic monomer is a lactone selected from the group consisting of ω-pentadecalactone, ω-dodecalactone, δ-valerolactone, lactide, glyocolide, β-propiolactone, ε-caprolactone, and γ-butyrolactone.

25. The process of claim 19, wherein said cyclic monomer is a carbonate selected from the group consisting of trimethylene carbonate, tetramethylene carbonate, and 2,2-dimethyl trimethylene carbonate.

26. An oligomer prepared by the process of claim 19.

27. A process for increasing the ring-opening polymerization rate of a cyclic monomer, the process comprising (a) combining the cyclic monomer, the enzyme, and an amount of water, under conditions and for a time sufficient to generate an oligomer, (b) wherein the ring-opening polymerization rate is increased by at least 20% when the amount of water is increased from about 0.20% to about 5.6%, and (c) wherein the cyclic monomer is a lactone or a cyclic carbonate.

\* \* \* \* \*